(12) United States Patent
Das

(10) Patent No.: US 8,137,311 B2
(45) Date of Patent: Mar. 20, 2012

(54) TEST METHOD AND APPARATUS FOR VERIFICATION OF MEDICAL DEVICE FUNCTIONALITY

(75) Inventor: Stephen D. Das, The Woodlands, TX (US)

(73) Assignee: The Alfred E. Mann Foundation For Scientific Research, Santa Clarita, CA (US)

(*) Notice: Subject to any disclaimer, the term of this patent is extended or adjusted under 35 U.S.C. 154(b) by 232 days.

(21) Appl. No.: 12/497,671

(22) Filed: Jul. 5, 2009

(65) Prior Publication Data

US 2009/0270805 A1    Oct. 29, 2009

Related U.S. Application Data

(62) Division of application No. 11/222,161, filed on Sep. 8, 2005, now Pat. No. 7,604,614.

(60) Provisional application No. 60/625,429, filed on Nov. 5, 2004.

(51) Int. Cl.
*A61M 5/00* (2006.01)

(52) U.S. Cl. ........... 604/111; 604/131; 604/151; 417/63

(58) Field of Classification Search .................. 604/111, 604/131, 151, 891.1; 417/63; 206/570, 363, 206/459.1; 73/168

See application file for complete search history.

(56) References Cited

U.S. PATENT DOCUMENTS

| | | | |
|---|---|---|---|
| 3,585,963 A | 6/1971 | Hiszpanski | |
| 3,722,537 A | 3/1973 | Gregerson et al. | |
| 4,274,285 A | 6/1981 | Purgold | |
| 4,384,470 A | 5/1983 | Fiore | |
| 4,423,732 A | 1/1984 | Tarjan et al. | |
| 4,588,085 A | 5/1986 | Sussman | |
| 4,605,007 A | 8/1986 | Heraly | |
| 4,721,123 A | 1/1988 | Cosentino et al. | |
| 4,830,005 A | 5/1989 | Woskow | |
| 5,237,991 A | 8/1993 | Baker et al. | |
| 5,383,338 A | 1/1995 | Bowsky et al. | |
| 6,292,697 B1 | 9/2001 | Roberts | |
| 6,467,506 B1 | 10/2002 | Nguyen | |
| 6,554,798 B1 | 4/2003 | Mann et al. | |
| 6,652,510 B2 | 11/2003 | Lord et al. | |
| 7,604,614 B2 | 10/2009 | Das | |
| 2002/0113606 A1 | 8/2002 | Hansen et al. | |
| 2003/0047128 A1 | 3/2003 | Delp | |
| 2004/0106874 A1 | 6/2004 | Eigler et al. | |
| 2005/0273059 A1 | 12/2005 | Mernoe et al. | |

*Primary Examiner* — Bhisma Mehta
(74) *Attorney, Agent, or Firm* — Henricks, Slavin & Holmes LLP

(57) ABSTRACT

This invention relates to methods, apparatuses and systems for testing the functionality of the pumping mechanism of a medical device, e.g., an implantable infusion pump, while the medical device is contained within a shipping package. The test apparatus enables such functional verification, without opening the shipping package, when the medical device is still contained within the package that has been appropriately sealed to maintain sterility of the medical device.

13 Claims, 4 Drawing Sheets

TEST METHOD AND APPARATUS FOR VERIFICATION OF MEDICAL DEVICE FUNCTIONALITY

RELATED APPLICATION

This application is a divisional of application Ser. No. 11/222,161, filed Sep. 8, 2005, now U.S. Pat. No. 7,604,614, which claims the benefit of U.S. Provisional Application 60/625,429, filed Nov. 5, 2004, which is incorporated herein by reference.

FIELD OF THE INVENTION

This invention relates to a method and apparatus for testing the functionality of a medical device, e.g., an implantable infusion pump, while the device is still contained within a sterile shipping package.

BACKGROUND OF THE INVENTION

Applications exist which require that devices be kept in a sterile package prior to use. For example, it is generally understood in the medical community that contaminants or infectious material should not be introduced into the human body. To that end, medical devices, and particularly devices intended for implantation in the body, such as infusion pumps, are preferably assembled under sterile conditions and shipped in packages which are appropriately sealed to maintain the sterile environment. Such packages generally remain sealed until they are opened immediately prior to surgically implanting the device.

It is, of course, important to verify that the device is operable, i.e., functional, prior to implanting. To assure the availability of at least one functional device, it is common practice to supply multiple devices to the surgical location prior to implantation. This practice can be inconvenient, can introduce delays in surgery, and can increase costs.

SUMMARY OF THE INVENTION

The present invention is directed to a method and apparatus which enables the functionality of a medical device for discharging fluid, e.g., an implantable infusion pump, to be verified while the device is contained in a sterile package. More particularly, the invention is concerned with medical devices which include an actuatable fluid transfer mechanism, e.g., a pump and/or valve mechanism.

In accordance with the invention, the medical device will be placed in a package prior to shipment from its place of manufacture. The package is then appropriately sealed to establish a sterile environment for the device. Subsequently, and before opening the package to access and use the device, the device is actuated, e.g., by an RF command signal transmitted from outside of the package, and the response of the device is then monitored. An indication is then produced, recognizable by a responsible user, to indicate whether the device is functional, i.e., whether or not the monitored response satisfies some predetermined criteria.

In a preferred embodiment, the medical device comprises an implantable infusion pump with a case and an outlet port (or "outlet"). A simple low cost test apparatus (or "indicator") is coupled to the outlet port of the infusion pump prior to placing the pump into the package. The test apparatus is configured to detect pump activity (e.g. a fluid discharge and/or a pressure change at the outlet port) and provide an indication thereof, e.g., visual and/or aural, recognizable by a responsible person. Prior to opening the package, the infusion pump is actuated (while still in the package) by a command signal generated by a transmitter externally of the package and communicated to a receiver within the infusion pump. In other words, an indicator may be located within the sealed interior and outside the pump case, in fluid communication with the outlet, and configured to provide an indication that is discernible outside the package in response to a fluid discharge at the outlet and/or a pressure change at the outlet.

A preferred test apparatus in accordance with the invention is coupled to an infusion pump's catheter outlet port and is configured to provide a visual indication in response to pump activity (i.e. fluid discharge and/or pressure change) at the outlet port. The indication is visible externally of the package through a transparent portion or window in the package. In other words, the indicator may be connected to the outlet and is configured to (or has an indication device that is configured to) provide a visible indication in response to a fluid discharge at the outlet and/or a pressure change at the outlet. Thus, without opening the sterile package, a responsible person can determine whether the pump is functioning in response to the externally generated command signal.

A preferred test apparatus in accordance with the invention includes an elongate tube having its open proximal end coupled to the pump's outlet port. The tube contains a column of gas, e.g., air, and a sealed distal end. As liquid is discharged from the outlet port into the tube, the liquid moves the gas/liquid interface, which can be visually observed by the responsible person through the window in the package.

In alternative embodiments of the invention, a flexible membrane, or a piston, can be coupled to the pump outlet port in lieu of the elongate tube to exhibit physical movement in response to a fluid discharge and/or pressure change from the port. In a further alternative embodiment, the visual indication can comprise a light source which can be activated in response to detected pump activity.

In a yet further alternative embodiment of the invention, the test apparatus can be configured to produce an aural indication in response to detected pump activity. For example, a buzzer, bell, chime, etc., can be activated to provide a sound recognizable by the responsible person.

In a still further embodiment, the test apparatus can transmit a signal externally of the package to indicate detected pump activity.

DETAILED DESCRIPTION

Figure 1:
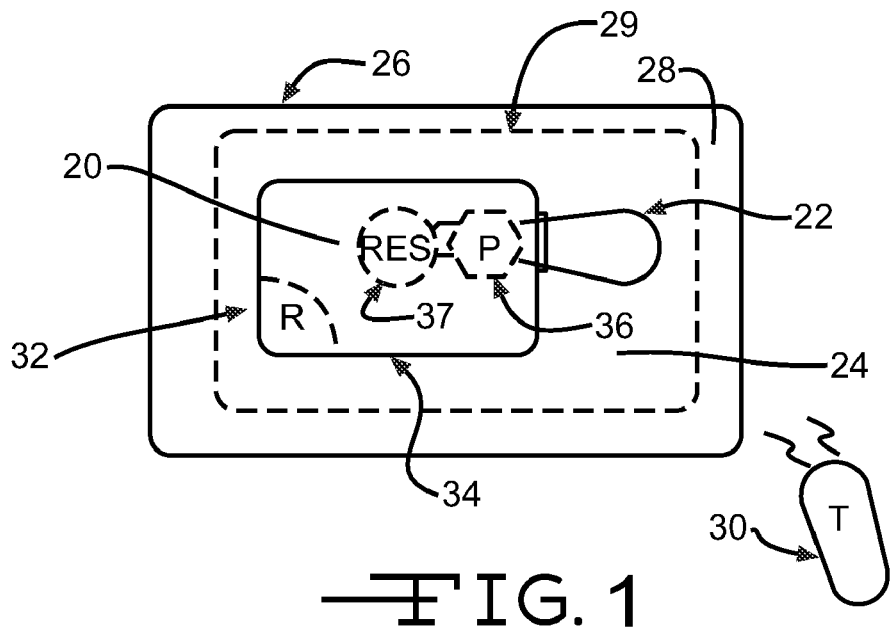
FIG. 1 is a block diagram of an exemplary implantable infusion pump, connected to a test apparatus in accordance with the invention, within a shipping package.

FIG. 1 illustrates an exemplary block diagram of a medical device, e.g., an implantable infusion pump 20, connected to a test apparatus 22 in accordance with the invention. The pump 20 and apparatus 22 are configured to be placed within an interior cavity 24 of a shipping package 26 that may be sufficiently transparent to permit viewing of movement of an indicator (discussed below) within the package. A transparent cover 28 overlays and appropriately seals the cavity 24 at its boundary 29 to maintain a sterile environment (i.e., a sterile sealed interior) within the shipping package 26 in the illustrated embodiment. Once the infusion pump 20 and test apparatus 22 are sealed in the shipping package 26, the functionality of the infusion pump 20 can be verified by transmitting a command signal, e.g., RF, from an external transmitter 30 to a receiver 32 within the case 34 of the implantable infusion pump 20.

Typical implanted infusion pumps include a receiver and/or transceiver for receiving telemetry data and critical signals from an external transmitter and for transmitting patient and/or infusion pump condition data to an external (non-implanted) control unit or monitoring station. It is contemplated that such a receiver and/or transceiver be used as the receiver 32 in accordance with the present invention. In response to the command signal, the receiver 32 actuates a fluid transfer device 36, e.g., a pumping mechanism, within the case 34 to transfer fluid, e.g., liquid, from a reservoir 37 in the case 34 for discharge through the infusion pump's 20 outlet port. The test apparatus 22 in accordance with the present invention functions to detect actuation of the mechanism 36, as by sensing whether a fluid discharge has occurred.

Figure 2:
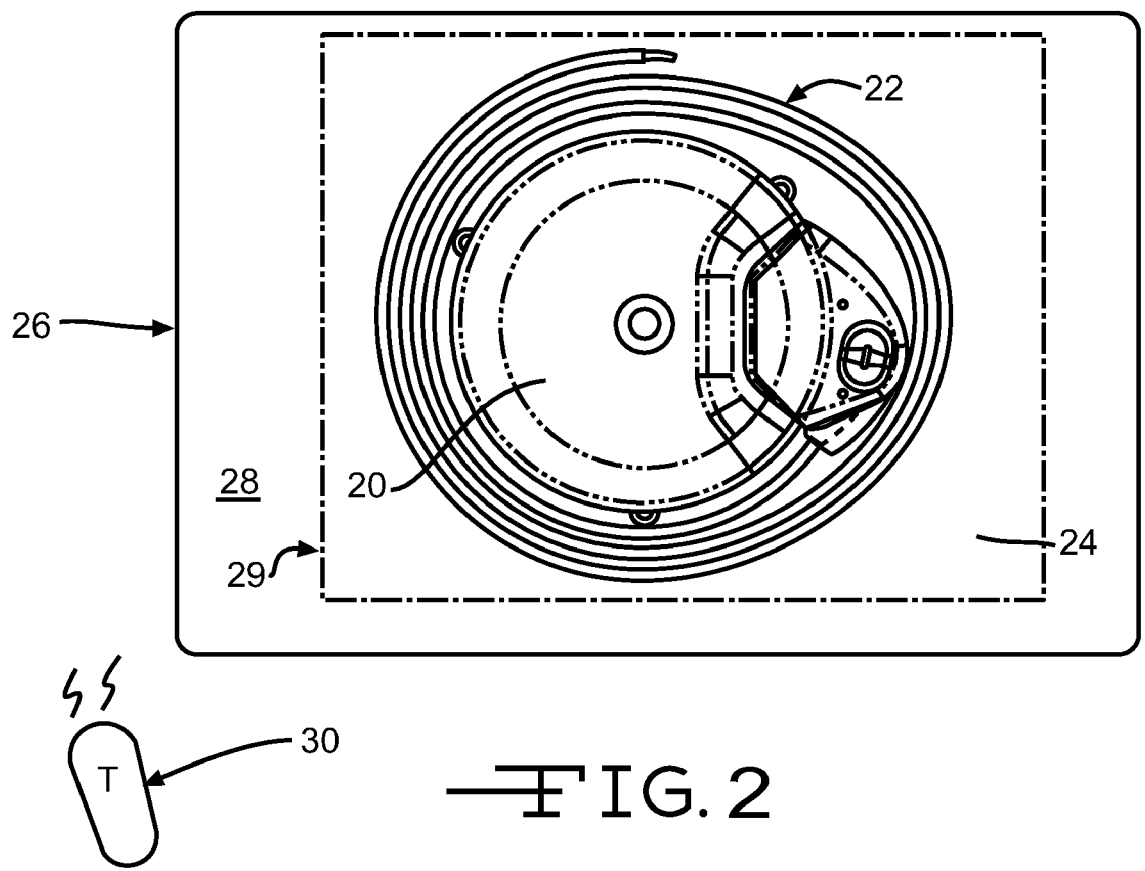
FIG. 2 is a plan view of an exemplary implantable infusion pump, connected to a test apparatus in accordance with the invention, within a shipping package.

FIG. 2 illustrates an exemplary implantable infusion pump 20 connected to a preferred test apparatus 22 in accordance with the invention. The infusion pump 20 and apparatus 22 are shown mounted in an exemplary sterile shipping package 26. The boundary seal 29 of the transparent cover 28 maintains the infusion pump 20 in a sterile environment preventing contamination unless the integrity of the transparent cover 28 or boundary seal 29 is compromised. The shipping package 26 schematically depicted in FIG. 2 is exemplary only but representative of various types of packaging which can be used with the test apparatus 22. Alternatively, the test apparatus 22 is suitable for use with any sealed bag or other container having a transparent area through which a visual indication produced by the test apparatus 22 can be viewed.

Figure 3:
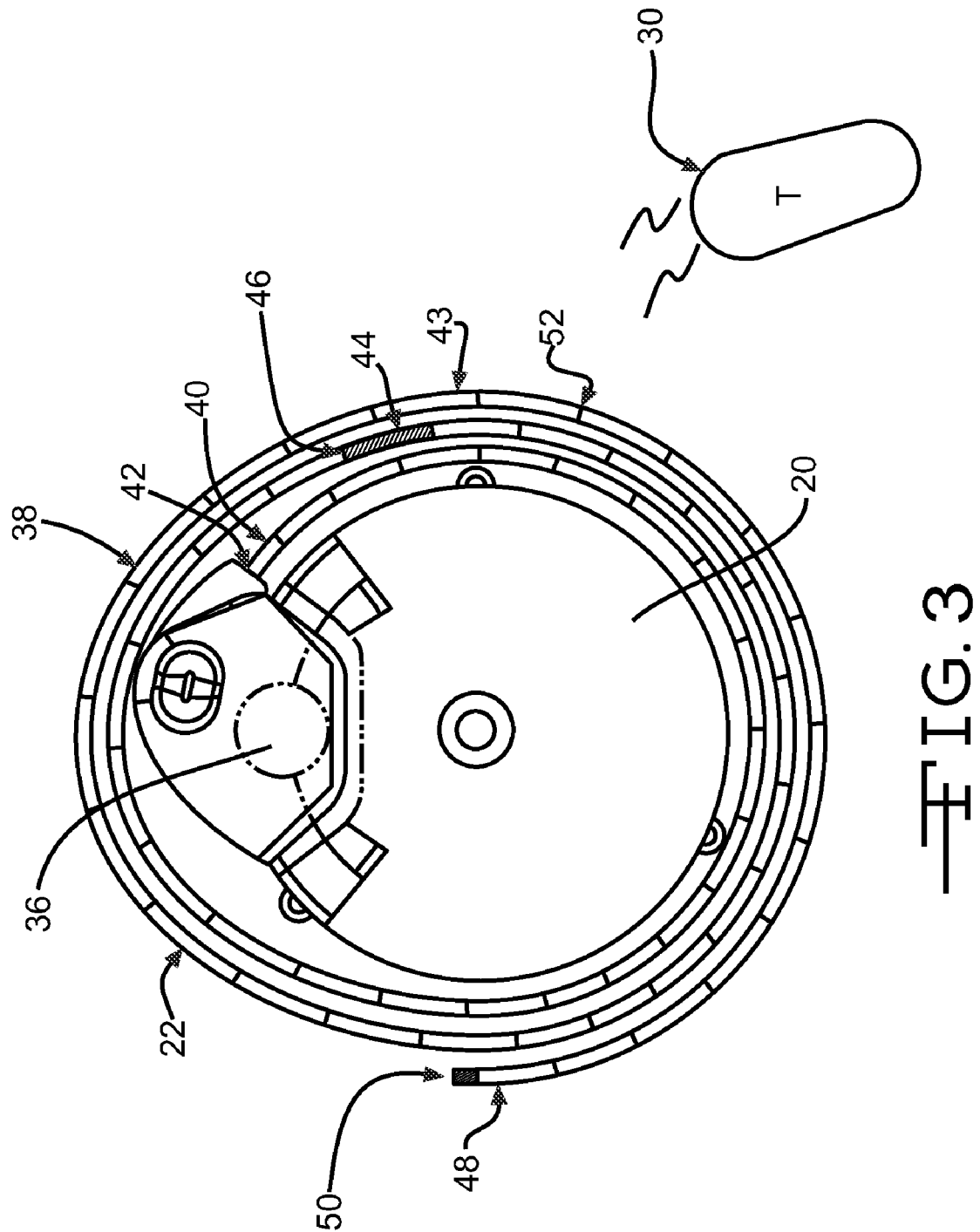
FIG. 3 is an enlarged plan view of the exemplary infusion pump of FIG. 2 (with the shipping package omitted) illustrating the test apparatus in greater detail.

Attention is now directed to FIG. 3 which illustrates in greater detail a preferred embodiment of the test apparatus of FIG. 2. The test apparatus 22 (or "indicator") comprises an indication device in the form of a tube that has sufficient transparency to enable fluid movement within the tube to be observed outside of the tube (e.g., the exemplary transparent tube 38) having a proximal end 40 attached to the catheter outlet port 42 of the infusion pump 20. When the receiver 32 (FIG. 1) receives a command signal from the transmitter 30, it actuates the pumping mechanism 36 to define an operating state which transfers liquid from reservoir 37 (FIG. 1) for discharge through the catheter outlet port 42 into the transparent tube 38. In other words, one exemplary indicator may be a tube that is connected to the outlet and is sufficiently transparent to permit a user to visually observe fluid movement within the tube. The movement of liquid through the tube 38 is visible through the transparent cover 28 and provides a visual indication of functionality of the infusion pump 20 to a responsible observer.

In a preferred embodiment, the tube 38 is filled with sterile liquid 43, e.g., the same liquid used to fill the reservoir 37 (FIG. 1) prior to shipment. The liquid in the tube 38 preferably contains a short column of gas, e.g., air 44. After filling, the tube 38 is attached to the catheter outlet port 42 of the implantable infusion pump 20. When the pumping mechanism 36 is actuated in response to a command signal received by receiver 32 (FIG. 1), liquid discharged from the outlet port 42 will move the liquid/gas interface 46 inside the tube 38. The movement of the interface 46 can be readily observed through transparent cover 28, indicating proper operation of the implantable infusion pump 20.

In most applications, it is preferable to seal the distal end 48 of the tube 38 with a cap/plug 50, of a material such as silicone, to prevent evaporation or leakage of liquid. If the tube 38 is sealed with a cap/plug 50, the tube 38 can be marked with calibration or volume marks 52 to indicate the actual volume of liquid pumped into tube 38. If leakage or evaporation is not an issue and the need to measure fluid discharge is not required, the distal end 48 of the tube 38 need not be sealed, so long as the tube has sufficient capacity to accommodate the liquid discharge.

The tubing 38 is preferably coiled around the implantable infusion pump 20 such that its entire length is visible through the transparent cover 28 (not shown in FIG. 3). The specific dimensions of the tube 38 can vary dependent upon the size of the implantable infusion pump 20. It must, of course, be long enough to accommodate a volume of discharged liquid sufficient to verify pump functionality. An exemplary tube length could be approximately 22 inches or roughly three times the circumference of the exemplary infusion pump 20. An exemplary tube inner diameter could be about 0.047 inches, approximately equal to the diameter of a catheter for which the outlet port 42 is sized.

Figure 4:
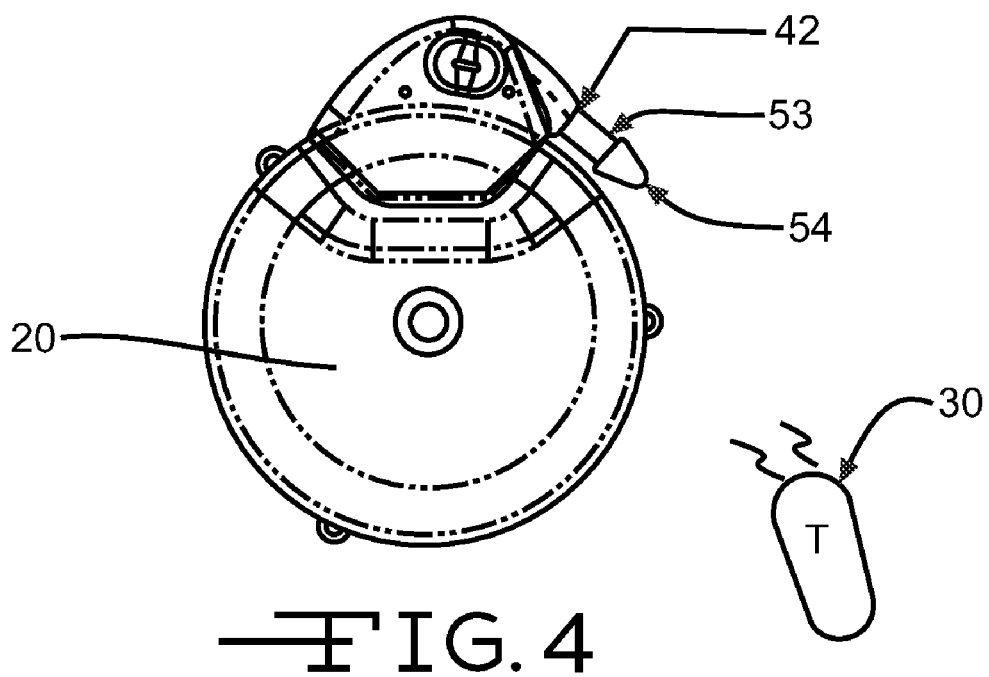
FIG. 4 is a plan view of an exemplary infusion pump connected to an alternative embodiment of the invention using a membrane.

Visual indications of pump activity can be produced in alternative ways. For example, FIG. 4 shows a test apparatus (or "indicator") that includes an indication device in the form of a short tube 53 coupling the outlet port 42 to a flexible (or "distendible") membrane 54. When the pump is activated to pump liquid out of port 42, the liquid discharge will cause the membrane 54 to distend. This membrane distention can be visually observed through the transparent cover 28 to indicate pump functionality.

Figure 5:
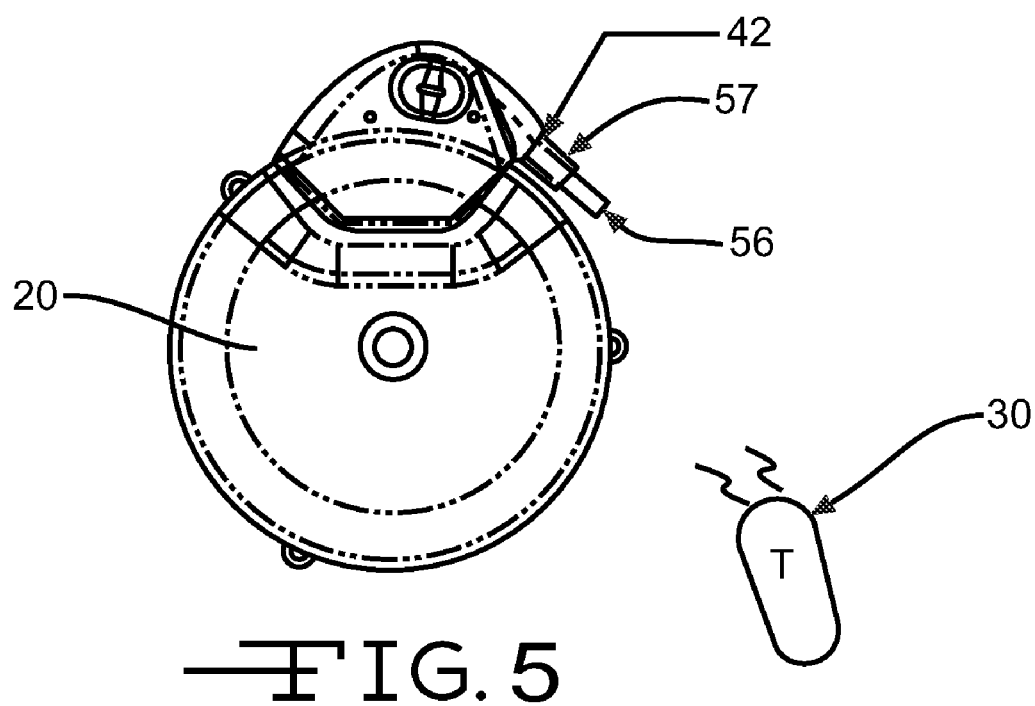
FIG. 5 is a plan view of an exemplary infusion pump connected to an alternative embodiment of the invention using a piston.

FIG. 5 illustrates another alternative visual indication embodiment of the test apparatus (or "indicator") in which indicator includes an indication device in the form of a slidable piston 56 that is used in lieu of the membrane 54 of FIG. 4. In FIG. 5, the liquid discharge from port 42 will produce a pressure on piston 56 which acts on the piston 56 to slide it outwardly from supporting sleeve 57.

Figure 6:
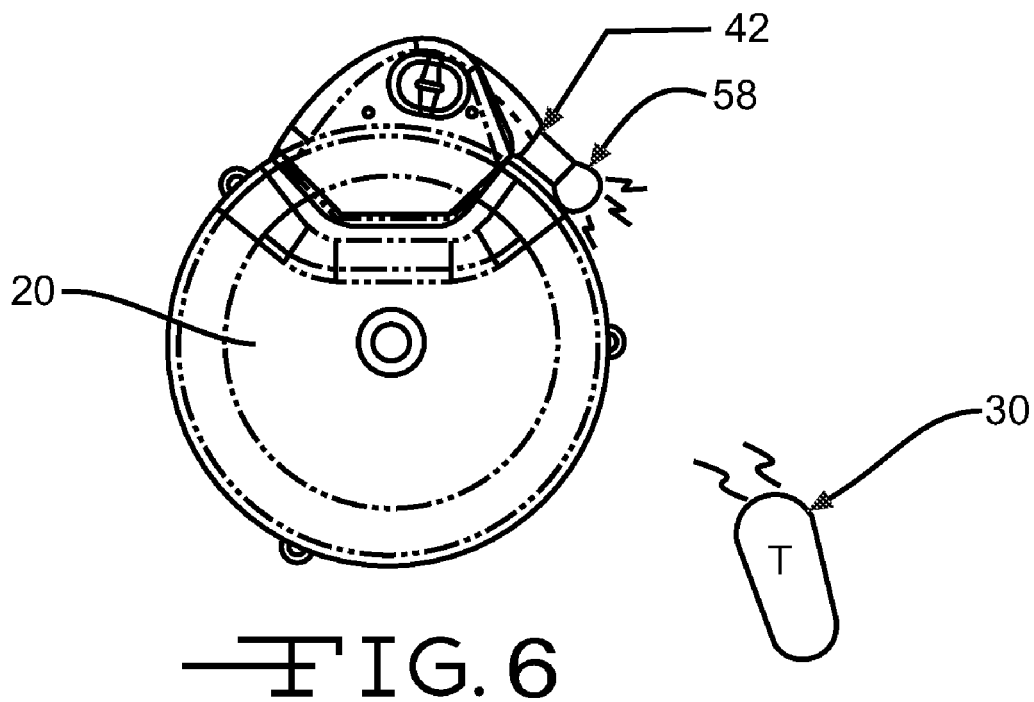
FIG. 6 is a plan view of an exemplary infusion pump connected to an alternative embodiment of the invention using a light source.

FIG. 6 illustrates a further alternative visual indication embodiment of the test apparatus (or "indicator") in which the indicator includes an indication device in the form of a light source and also includes a switch. Liquid discharged from port 42 operates a switch (not shown) to activate a light source 58 which can be visually observed through the transparent cover 28 to indicate pump functionality.

Figure 7:
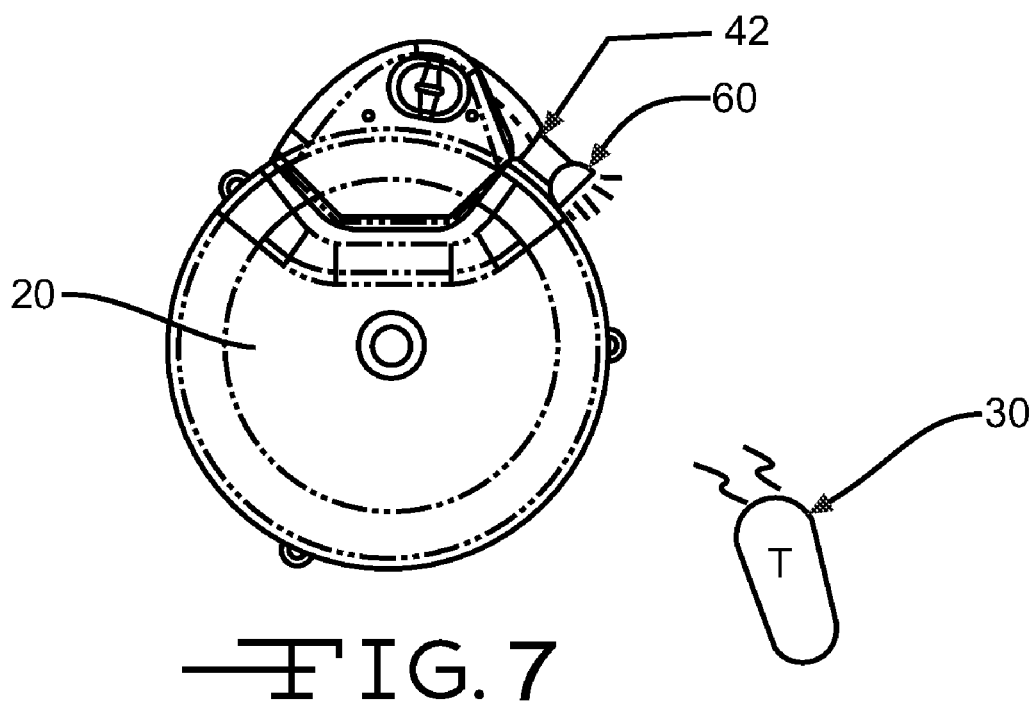
FIG. 7 is a plan view of an exemplary implantable infusion pump connected to a further alternative embodiment of the invention using a sound source.

FIG. 7 depicts a still further embodiment of the test apparatus (or "indicator") in which the indicator includes an indication device in the form of a sound generator (or "source") 60, e.g., a buzzer, chime, etc., for responding to liquid discharge from port 42 to produce an audible signal.

In a still further alternative embodiment, the sensing of pump activity after receipt of an externally transmitted command signal causes a transceiver internal to the infusion pump to transmit an indicating signal externally of the sterile package. This indicating signal can then be recognized by an external (non-implanted) control unit or other monitoring device to alert the responsible person.

From the foregoing, it should now be appreciated that an inexpensive test apparatus has been described for testing the functionality of an infusion pump while still contained in its sterile shipping package. Although only a limited number of embodiments have been illustrated, it is recognized that variations and modifications will occur to those skilled in the art coming within the spirit and scope of the invention as defined by the appended claims.

The invention claimed is:

1. An apparatus, comprising
a package including a sealed interior;
an infusion pump, including a pump case, a fluid transfer device within the pump case and an outlet that receives fluid from the fluid transfer device, located within the sealed interior of the package; and
an indicator located within the sealed interior and outside the pump case, in fluid communication with the outlet, and configured to provide an indication that is discernible outside the package in response to a fluid discharge at the outlet and/or a pressure change at the outlet.

2. An apparatus as claimed in claim 1, wherein the sealed interior comprises a sterile sealed interior.

3. An apparatus as claimed in claim 1, wherein the outlet comprises a catheter outlet port.

4. An apparatus as claimed in claim 1, wherein
the indicator is visible through the package; and
the indicator is configured to provide a visible indication in response to a fluid discharge at the outlet and/or a pressure change at the outlet.

5. An apparatus as claimed in claim 4, wherein the indicator is selected from the group consisting of a distendible membrane and a slidable piston.

6. An apparatus as claimed in claim 4, wherein the indicator comprises a tube that is connected to the outlet and is sufficiently transparent to permit a user to visually observe fluid movement within the tube.

7. An apparatus as claimed in claim 4, wherein the indicator includes a light source.

8. An apparatus as claimed in claim 1, wherein the indicator includes a sound source.

9. An apparatus as claimed in claim 1, wherein
the infusion pump includes a reservoir located within the pump case; and
the reservoir, fluid transfer device and outlet are arranged such that fluid flows from the reservoir to the outlet.

10. An apparatus as claimed in claim 9, wherein the fluid transfer device comprises a pump mechanism.

11. An apparatus as claimed in claim 1, wherein the infusion pump is configured to be surgically implanted after being removed from the package.

12. An apparatus as claimed in claim 1, wherein the package comprises a shipping package.

13. An apparatus as claimed in claim 12, wherein the infusion pump comprises an implantable infusion pump.

* * * * *